US00PP13977P29

(12) United States Plant Patent
van Zoest

(10) Patent No.: US PP13,977 P2
(45) Date of Patent: Jul. 15, 2003

(54) CLEMATIS PLANT NAMED 'NEW LOVE'

(75) Inventor: Jan van Zoest, Boskoop (NL)

(73) Assignee: Jan van Zoest B.V., Boskoop (NL)

( * ) Notice: Subject to any disclaimer, the term of this patent is extended or adjusted under 35 U.S.C. 154(b) by 0 days.

(21) Appl. No.: 10/139,955

(22) Filed: May 6, 2002

(51) Int. Cl.[7] ..... A01H 5/00

(52) U.S. Cl. ..... Plt./228
(58) Field of Search ..... Plt./228

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Clematis plant named 'New Love', characterized by its upright growth habit; freely branching habit; freely flowering habit; and large single and semi-double flowers that are pink in color.

1 Drawing Sheet

BOTANICAL CLASSIFICATION/CULTIVAR DESIGNATION

*Clematis L.* cultivar New Love.

BACKGROUND OF THE INVENTION

The present Invention relates to a new and distinct cultivar of Clematis plant, botanically known as *Clematis L.,* and hereinafter referred to by the name 'New Love'.

The new cultivar originated from a random cross-pollination of two unidentified selections of *Clematis L.,* not patented, in Boskoop, The Netherlands. The new cultivar was discovered and selected by the Inventor as a flowering plant within the progeny from this cross-pollination in a controlled environment in Boskoop, The Netherlands, in 1996.

Asexual reproduction of the new cultivar by cuttings taken in Boskoop, The Netherlands, since 1997, has shown that the unique features of this new Clematis are stable and reproduced true to type in successive generations.

SUMMARY OF THE INVENTION

Plants of the cultivar New Love have not been observed under all possible environmental conditions. The phenotype may vary somewhat with variations in environment such as temperature and light intensity without, however, any variance in genotype.

The following traits have been repeatedly observed and are determined to be the unique characteristics of 'New Love'. These characteristics in combination distinguish 'New Love' as a new and distinct cultivar of Clematis:

1. Upright and compact growth habit.
2. Strong stems.
3. Single violet-colored flowers.

Plants of the new Clematis differ primarily from plants of the unidentified parent selections primarily in flower color.

Plants of the new Clematis can be compared to plants of the *Clematis heraclefolia* cultivar Wyevale, not patented. In side-by-side comparisons conducted in Boskoop, The Netherlands, plants of the new Clematis differed from of the cultivar Wyevale in the following characteristics:

1. Plants of the new Clematis were more compact than plants of the cultivar Wyevale.

2. Flowers of plants of the new Clematis are darker violet in color than flowers of plants of the cultivar Wyevale.

3. Flowers of plants of the new Clematis are not as fragrant as flowers of plants of the cultivar Wyevale.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Clematis. The photograph comprises a side perspective view of a typical flowering plant of 'New Love'.

DETAILED BOTANICAL DESCRIPTION

In the following description, color references are made to The Royal Horticultural Society Colour Chart, 2001 Edition, except where general terms of ordinary dictionary significance are used. Plants used for the photograph and the following description were about two years old and were grown in 1.5-liter containers in an outdoor nursery in Boskoop, The Netherlands. The following measurements and values represent averages taken from a group of typical flowering plants during the late summer.

Botonical classification: *Clematis L.* cultivar New Love.

Parentage:

*Female, or seed, parent.*—Unidentified selection of *Clematis L.,* not patented.

*Male, or pollen, parent.*—Unidentified selection of *Clematis L.,* not patented.

Propagation:

*Type.*—By cuttings.

*Time to initiate roots.*—About 30 days at 20 to 25° C.

*Time to produce a rooted young plant.*—About 42 days at 20 to 25° C.

*Root description.*—Numerous, fibrous, freely branching.

Plant description:

*Form.*—Perennial flowering subshrub; compact and upright plant habit; broad inverted triangle. Plants are basal branching with typically about two main stems per plant. Moderately vigorous growth habit.

*Plant height* (*length*).—About 70 cm.

*Plant diameter.*—About 40 cm.

*Stems.*—Length: About 65 cm. Diameter: About 5 mm. Internode length: About 25 cm. Shape: Round in cross-section. Strength: Strong. Texture: Densely pubescent. Color: 143A to 143B.

*Foliage description.*—Arrangement: Opposite; compound; three leaflets per leaf. Length, terminal leaflet: About 10 cm. Length, lateral leaflets: About 7.5 cm. Width, terminal leaflet: About 8 cm. Width, lateral leaflets: About 4 cm. Shape, terminal leaflet: Broadly elliptic. Shape, lateral leaflets: Ovate. Apex, terminal leaflet: Acute. Apex, lateral leaflets: Acuminate. Base, terminal and lateral leaflets: Cuneate. Margin, terminal and lateral leaflets: Serrate with occasional shallow lobes. Texture, terminal and lateral leaflets, upper and lower surfaces: Slightly rugose; sparsely pubescent. Venation pattern, terminal and lateral leaflets: Pinnate. Petiole length, leaf: About 12 cm. Petiole diameter, leaf: About 4 mm. Color, terminal and lateral leaflets: Developing leaves, upper surface: Slightly lighter than 139A. Developing leaves, lower surface: 137C. Fully expanded leaves, upper surface: Slightly darker than 137A. Fully expanded leaves, lower surface: 137C. Venation, upper and lower surfaces: 144A. Petiole: 144A; towards the base of the leaflets, N186C.

Flower description:

*Flower type and habit.*—Single salverform flowers arranged singly in terminal and axillary cymes; about 30 flowers per cyme and about five cymes per stem in flower at one time. Flowers face upright to outward. Flowers not persistent.

*Natural flowering season.*—Flowering continuous from the end of May until September in Boskoop, The Netherlands.

*Flower longevity on the plant.*—About one week.

*Fragrance.*—Moderate; pleasant and sweet.

*Inflorescence height.*—About 4 cm.

*Inflorescence diameter.*—About 6.5 cm.

*Flower diameter.*—About 2.5 cm.

*Flower depth* (*height*).—About 1.9 cm.

*Flower buds.*—Length: About 1.9 cm. Diameter: About 6 mm. Shape: Ovoid to flattened globular. Color: 92A to 94C.

*Petals.*—None observed.

*Sepals.*—Quantity per flower: Four. Length: About 2.3 cm. Width: About 5 mm. Shape: Oblanceolate to somewhat spatulate. Apex: Acute. Base: Attenuate. Margin: Entire; undulate. Texture, upper surface: Glabrous, slightly rugose. Texture, lower surface: Glabrous, smooth. Color, single flowers: When and fully opened, upper surface: 94B. When and fully opened, lower surface: 94B to 85A.

*Peduncles.*—Length: About 2.5 cm. Diameter: About 3 mm. Angle: About 15 to 45° from vertical. Strength: Strong. Color: 143A to 143B occasionally tinged with N186C.

*Pedicels.*—Length: About 5 mm. Diameter: About 1.5 mm. Angle: Erect to about 80° from vertical. Strength: Strong. Color: 138C.

*Reproductive organs.*—Stamens: Quantity per flower: About 20. Anther shape: Oblong. Anther length: About 7 mm. Anther color: 4C. Amount of pollen: Scarce. Pollen color: 4C to 4D. Pistils: Quantity per flower: About 10. Pistil length: About 3 mm. Stigma shape: Narrowly club-shaped. Stigma color: Close to 138C. Style length: About 2.8 mm. Style color: 157D. Ovary color: 138D.

*Fruit.*—Quantity per plant: About 20. Type: Achene. Length: About 1.7 cm. Diameter: About 1.5 cm. Color: Brown, close to N200A to N200B.

*Seed.*—Length: About 2.5 mm. Diameter: About 2 mm. Color: Brown, close to N200A to N200B.

Disease/pest resistance: Plants of the new Clematis have not been noted to be resistant to pathogens and pests common to Clematis.

Weather tolerance: Plants of the new Clematis have been observed to be tolerant to rain and wind and tolerant to temperatures from −20 to 40° C.

It is claimed:

1. A new and distinct cultivar of Clematis plant named 'New Love', as illustrated and described.

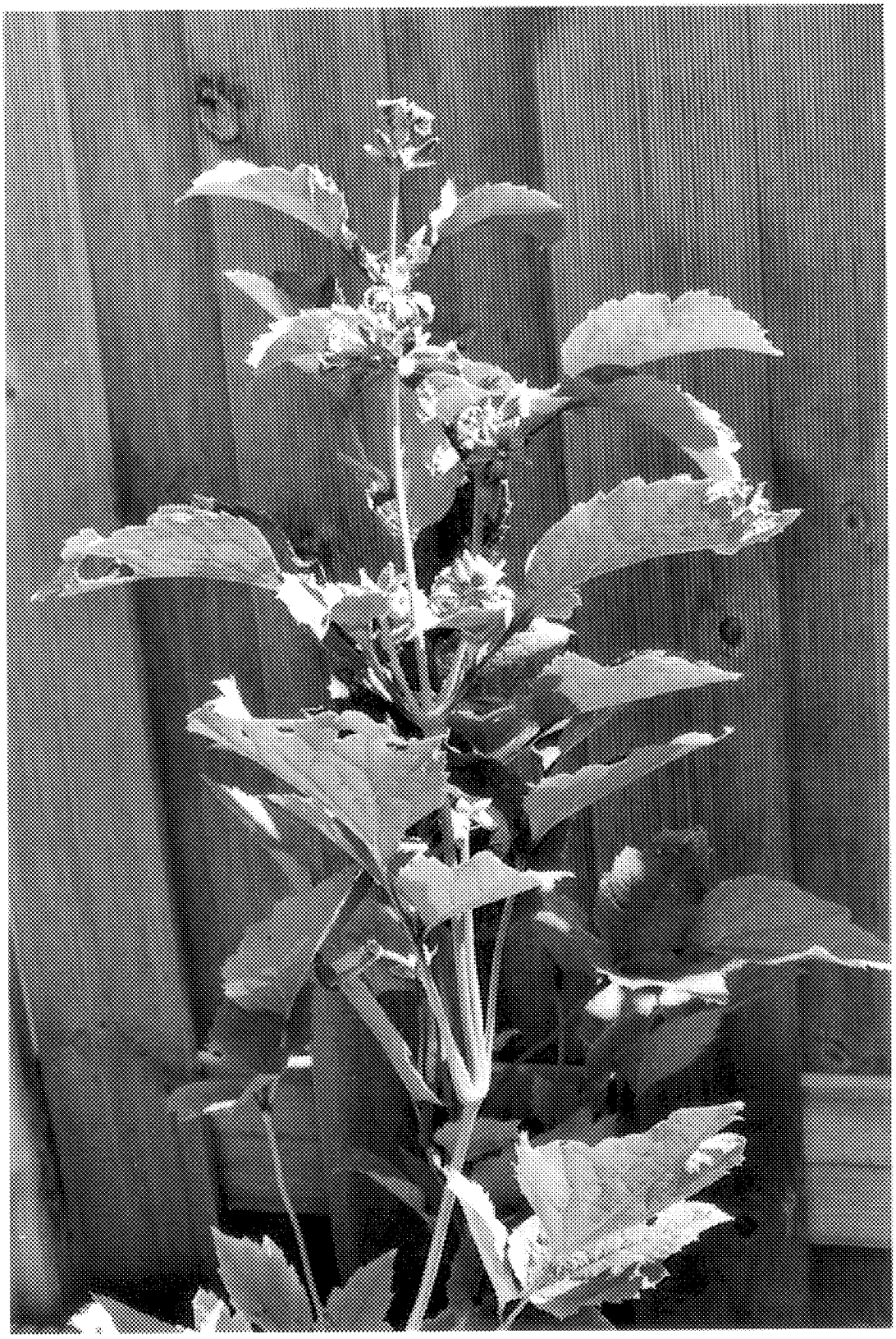

* * * * *